United States Patent [19]

Duff et al.

[11] Patent Number: 5,756,744
[45] Date of Patent: May 26, 1998

[54] UNSYMMETRICAL PERYLENE DIMERS

[75] Inventors: James M. Duff, Mississauga; C. Geoffrey Allen, Waterdown; Ah-Mee Hor; Gordon K. Hamer, both of Mississauga, all of Canada

[73] Assignee: Xerox Corporation, Stamford, Conn.

[21] Appl. No.: 902,458

[22] Filed: Jul. 29, 1997

Related U.S. Application Data

[62] Division of Ser. No. 810,159, Feb. 26, 1997, Pat. No. 5,683,842.

[51] Int. Cl.$^6$ .................. C07D 471/02; C07D 471/06
[52] U.S. Cl. .................. 546/34; 546/36; 546/37
[58] Field of Search .................. 546/34, 36, 37

[56] References Cited

U.S. PATENT DOCUMENTS 5,645,965  7/1997  Duff ................................ 430/59

*Primary Examiner*—C. Warren Ivy
*Assistant Examiner*—D. Margaret M. Mach
*Attorney, Agent, or Firm*—E. O. Palazzo

[57] ABSTRACT

Photoconductive imaging members comprised of unsymmetrical dimeric perylene as a charge generator, wherein said perylene is of the following formula

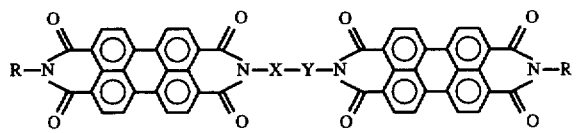

wherein R is hydrogen, alkyl, cycloalkyl, substituted alkyl, aryl, substituted aryl, aralkyl or substituted aralkyl group, and X—Y is an unsymmetrical bridging moiety of alkylene, substituted alkylene, arylene, substituted arylene, aralkylene or substituted aralkylene.

3 Claims, No Drawings

UNSYMMETRICAL PERYLENE DIMERS

This application is a division of application Ser. No. 08/810,159, filed Feb. 26, 1997, U.S. Pat. No. 5,683,842.

PENDING APPLICATION

There is illustrated in copending application U.S. Ser. No. 700,326, the disclosure of which is totally incorporated herein by reference, photoconductive imaging members with symmetrical dimeric perylenes.

BACKGROUND OF THE INVENTION

The present invention is directed generally to dimeric perylene pigments, and more specifically, to unsymmetrical perylene bisimide dimers of the formula

FORMULA 1

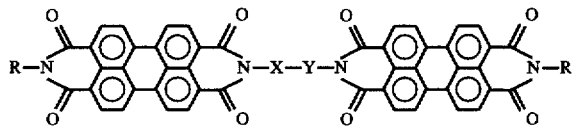

wherein R is hydrogen, alkyl, cycloalkyl, substituted alkyl, aryl, substituted aryl, aralkyl, substituted aralkyl, and the like, and X-Y, which X-Y can be represented by a single Z, represents an unsymmetrical bridging moiety such as alkylene, substituted alkylene, arylene, substituted arylene, aralkylene or substituted aralkylene. Alkyl includes linear and branched components with, for example, from 1 to about 25, and preferably from 1 to about 10 carbon atoms, such as methyl, ethyl, propyl, butyl, pentyl, heptyl, octyl, decyl, and the like. Cycloalkyl includes homologous rings from, for example, cyclopropane to cyclododecane. Substituted alkyl groups contain substituents such as hydroxy, alkoxy, carboxy, cyano, dialkylamino and the like. Aryl includes components with, for example, from 6 to about 24 carbon atoms such as phenyl, naphthyl, biphenyl, terphenyl and the like. Substituted aryl groups contain, for example, one to five substituents such as alkyl like methyl, or tertiary-butyl, halogen (fluoro, chloro, bromo, and iodo), hydroxy, alkoxy like methoxy, nitro, cyano and dimethylamino. Aralkyl includes components with from 7 to about 24 carbon atoms such as benzyl, phenethyl, fluorenyl and the like. Substituted aralkyl groups can contain the same substituents as the aforementioned aryl groups, and more specifically, for example, methyl, tertiary-butyl, halogen, hydroxy, methoxy, nitro and dialkylamino.

Unsymmetrical bridging groups X-Y, (Z) include alkylene such as 1,2-propylene, 1-methyl-1,3-propylene, 1-ethyl-1,3-propylene, 1-methyl-1,4-tetramethylene, 2-methyl-1,4-tetramethylene, 1-methyl-1,5-pentamethylene, 2-methyl-1,5-pentamethylene and higher unsymmetric alkylene groups with up to about 20 carbon atoms. Unsymmetric substituted alkylenes include, for example, 3-hydroxy-1,2-propylene, 2-hydroxy-1,4-tetramethylene, 2-methoxy-1,4-tetramethylene, 2-carboxy-1,4-tetramethylene and 2-dimethylamino-1,4-tetramethylene. Arylene denotes unsymmetrically substituted bridging groups including 2,4-, 2,3'-, 2,4'-, and 3,4'-biphenylene, and 1,3-, 1,6- and 1,7-naphthylene. Substituted arylenes include groups such as 2-chloro-1,4-phenylene, 2-methyl-4,4'-biphenylene, N-phenylbenzamide-3,4'-diyl, diphenylsulfone-3,4'-diyl and diphenylether-3,4'-diyl. Aralkylene includes benzyl-, phenethyl-, phenylpropyl- and fluorenyl-groups in which one perylene bisimide moiety is bonded to the alkyl group and the second is bonded to the 2-, 3- or 4- position of the aromatic ring. Substituted aralkylene includes groups of the aforementioned class in which substituents such as methyl, tertiary-butyl, halogen (fluoro, chloro, bromo, and iodo), hydroxy, methoxy, nitro, cyano and dimethylamino are attached to the aromatic ring. Examples of the unsymmetrical bridging X-Y or Z groups are illustrated hereinafter.

Embodiments of the present invention include a process for the preparation of the unsymmetrical perylene bisimide dimers in high yield and high purity, which process comprises the reaction of preferably at least two parts of a perylene monoimido anhydride of the following Formula 2, with an unsymmetrical diamine in a high boiling solvent, such as N-methylpyrrolidine, and washing the resultant product with hot solvents to remove residual starting components and other byproducts.

FORMULA 2
Perylene Monoimido Anhydride

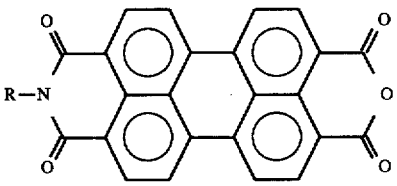

wherein R represents the groups or substituents described in Formula 1.

The unsymmetrical perylene dimers illustrated herein can be selected as a photoactive component in photoconductive imaging members used in electrophotographic printing, organic solar cells and, because of the asymmetry induced by the bridging moiety, they are expected to possess non-linear optical properties. Moreover, in embodiments the unsymmetrical dimers can be selected as a colorant in polymeric composite materials such as plastic objects, xerographic toners, and the like. The perylenes of Formula 1 can be selected, it is believed, as a component for solid state devices such as in solar cells, chemical sensors, electroluminescent devices and non-linear optical devices. They can also be used as dispersed colorants for coloration of, for example, plastics.

Important embodiments of the present invention include photoconductive imaging members comprised of a supporting substrate, a photogenerating layer comprised of the perylene dimer pigments illustrated herein of Formula 1 and a charge transport layer. Furthermore, the perylene dimer pigments are highly colored and can be prepared with a variety of hues such as orange, red, magenta, maroon, brown, black, greenish black, and the like depending, for example, on the R and X-Y substituents.

With the present invention in embodiments, photoconductive imaging members with the perylene dimer pigments obtained by coupling two perylene monomers together via an unsymmetrical bridging group (X-Y in Formula 1) enable a number of advantages with respect, for example, to photoconductive imaging members with monomeric perylene pigments or with symmetrical dimeric perylene pigments described in U.S. Ser. No. 700,326. For example, as indicated hereinafter the dimer of Formula 1, wherein R=n-pentyl and X-Y is 2-methyl-1,5-pentamethylene, possesses substantially higher photosensitivity than the related monomeric perylene pigment typified by a general Formula 3a, with two pentyl groups or the corresponding symmetrical dimer represented by Formula 1 wherein R=n-pentyl and X-Y is the symmetrical 1,6-hexamethylene group.

In embodiments, the present invention is directed to photogenerating pigments comprised of unsymmetrical perylene bisimide dimers. Embodiments of the present invention are directed to an imaging member comprised of a supporting substrate, a photogenerating layer comprised of an unsymmetrical perylene dimer of Formula 1 and, more specifically, wherein where R=n-propyl, n-butyl, isobutyl, n-pentyl, 2-methylbutyl, 3-methylbutyl, n-hexyl, n-heptyl and n-octyl and X-Y =2-methyl-1,4-tetramethylene, 2-methyl-1,5-pentamethylene, toluene-a-4-diyl, ethylbenzene-b-4-diyl, diphenyl ether-3,4'-diyl and the like, and a charge, especially hole, transport layer. More specifically, the unsymmetrical perylene dimers of the present invention are comprised of two different perylene bisimide molecules having the same terminal substituent (R group in Formula 1) wherein the two perylene moieties are distinguishable by being bonded to different ends of the unsymmetrical —X-Y— bridging group. The perylenes of the present invention can be characterized as having no center of symmetry. Imaging members with the photogenerating pigments of the present invention are sensitive to wavelengths of from about 400 to about 650 nanometers, that is in the visible region of the light spectrum. In embodiments thereof, the imaging members of the present invention generally possess broad spectral response to white light or, specifically to red, green and blue light emitting diodes and stable electrical properties over long cycling times. Many of the unsymmetrical perylene bisimide dimers of the present invention when selected as photogenerator pigments, exhibit excellent charge acceptance of about 800 volts surface potential in a layered device, dark decay of less than about 50 volts per second, for example 35 to 45, photosensitivities ranging from $E_{1/2}$ of about 4 to about 20 ergs/centimeter, excellent dispersibility and low solubility in typical coating compositions, such as solutions of certain polymers in organic solvents, such as methylene chloride, selected for the preparation of layered photoresponsive imaging members.

PRIOR ART

Generally, layered photoresponsive imaging members are described in a number of U.S. patents, such as U.S. Pat. No. 4,265,900, the disclosure of which is totally incorporated herein by reference, wherein there is illustrated an imaging member comprised of a photogenerating layer, and an aryl amine hole transport layer. Examples of photogenerating layer components include trigonal selenium, metal phthalocyanines, vanadyl phthalocyanines, and metal free phthalocyanines. Additionally, there is described in U.S. Pat. No. 3,121,006 a composite xerographic photoconductive member comprised of finely divided particles of a photoconductive inorganic compound dispersed in an electrically insulating organic resin binder. The binder materials disclosed in the '006 patent comprise a material which is substantially incapable of transporting for any significant distance injected charge carriers generated by the photoconductive particles.

The selection of selected perylene pigments as photoconductive substances is also known. There is thus described in Hoechst European Patent Publication 0040402, DE3019326, filed May 21, 1980, the use of N,N'-disubstituted perylene-3,4,9,10-tetracarboxyidiimide pigments as photoconductive substances. Specifically, there is, for example, disclosed in this publication N,N'-bis(3-methoxypropyl)perylene-3,4,9,10-tetracarboxyldiimide dual layered negatively charged photoreceptors with improved spectral response in the wavelength region of 400 to 700 nanometers. A similar disclosure is presented in Ernst Gunther Schlosser, *Journal of Applied Photographic Engineering*, Vol. 4, No. 3, page 118 (1978). There are also disclosed in U.S. Pat. No. 3,871,882 photoconductive substances comprised of specific perylene-3,4,9,10-tetracarboxylic acid derivative dyestuffs. In accordance with the teachings of this patent, the photoconductive layer is preferably formed by vapor depositing the dyestuff in a vacuum. Also, there is specifically disclosed in this patent dual layer photoreceptors with perylene-3,4,9,10-tetracarboxylic acid diimide derivatives, which have spectral response in the wavelength region of from 400 to 600 nanometers. Further, in U.S. Pat. No. 4,555,463, the disclosure of which is totally incorporated herein by reference, there is illustrated a layered imaging member with a chloroindium phthalocyanine photogenerating layer. In U.S. Pat. No. 4,587,189, the disclosure of which is totally incorporated herein by reference, there is illustrated a layered imaging member with a nonhalogenated perylene pigment photogenerating component. Both of the aforementioned patents disclose an aryl amine component as a hole transport layer.

Moreover, there are disclosed in U.S. Pat. No. 4,419,427 electrographic recording media with a photosemiconductive double layer comprised of a first layer containing charge carrier perylene diimide dyes, and a second layer with one or more compounds which are charge transporting materials when exposed to light, reference the disclosure in column 2, beginning at line 20. The two general types of monomeric perylene pigment, illustrated as follows in Formula 3, are commonly referred to as perylene bis(imides) and bis (imidazo) perylenes.

FORMULA 3
Perylene Bisimide (3a) and Bisimidazo (3b) Pigments

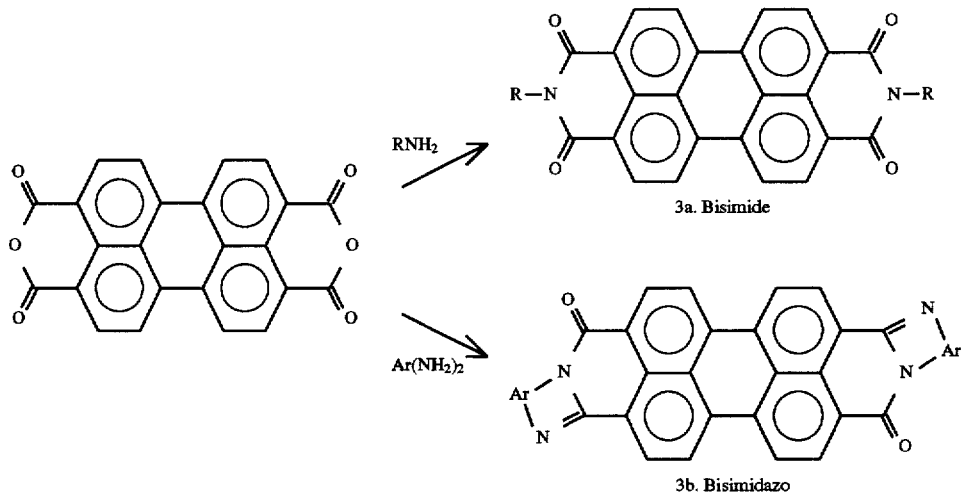

3a. Bisimide

3b. Bisimidazo wherein R=alkyl, aryl, aralkyl, etc.; Ar=1,2-phenylene, 18-naphthalene, and the like.

These perylenes can be prepared by reacting perylene tetracarboxylic acid dianhydride with primary amines or with diamino-aryl or alkyl compounds. Their use as photoconductors is disclosed in U.S. Pat. Nos. 3,871,882, the disclosure of which is totally incorporated herein by reference, and 3,904,407. The '882 patent discloses the use of the perylene dianhydride and bisimides in general (Formula 3a, R=H, lower alkyl (C1 to C4), aryl, substituted aryl, aralkyl, a heterocyclic group or the NHR' group in which R' is phenyl, substituted phenyl or benzoyl) as vacuum evaporated thin charge generation layers (CGLs) in photoconductive devices coated with a charge transporting layer (CTL). The '407 patent, the disclosure of which is totally incorporated herein by reference, illustrates the use of bisimide compounds (Formula 3a, R=alkyl, aryl, alkylaryl, alkoxyl or halogen, or heterocyclic substituent) with preferred pigments being R=chlorophenyl or methoxyphenyl. This patent illustrates the use of certain vacuum evaporated perylene pigments or a highly loaded dispersion of pigment in a binder resin as charge generating layer (CGL) in layered photoreceptors with a CTL overcoat or, alternatively, as a single layer device in which the perylene pigment is dispersed in a charge transporting active polymer matrix. The use of purple to violet dyestuffs with specified chromaticity values, including bisimidazo perylenes, specifically cis and trans bis(benzimidazo)perylene (Formula 3b, X=1,2-phenylene) and bis(1,8-naphthimidazo)perylene (Formula 3b, X=1,8-naphthylene), is disclosed in U.S. Pat. No. 3,972,717. This patent also describes the use of vacuum-evaporated CGLs in layered photoconductive devices. The use of a plurality of pigments, inclusive of perylenes, in vacuum evaporated CGLs is illustrated in U.S. Pat. No. 3,992,205.

U.S. Pat. No. 4,419,427 discloses the use of highly-loaded dispersions of perylene bisimides, with bis(2,6-dichlorophenylimide) being a preferred material, in binder resins as CGL layers in devices overcoated with a charge transporting layer such as a poly(vinylcarbazole) composition. U.S. Pat. No. 4,429,029 illustrates the use, in devices similar to those of the '427 patent, of bisimides and bisimidazo perylenes in which the perylene nucleus is halogenated, preferably to an extent where 45 to 75 percent of the perylene ring hydrogens have been replaced by halogen. U.S. Pat. No. 4,587,189, the disclosure of which is totally incorporated herein by reference, illustrates layered photoresponsive imaging members prepared with highly-loaded dispersions or, preferably, vacuum evaporated thin coatings of cis- and trans-bis(benzimidazo)perylene (3a, X=1,2-phenylene) and other perylenes overcoated with hole transporting compositions comprised of a variety of N,N, N',N'-tetraaryl-4,4'-diaminobiphenyls. U.S. Pat. No. 4,937,164 illustrates the use of perylene bisimides and bisimidazo pigments in which the 1,12 and/or 6,7 position of the perylene nucleus is bridged by one or two sulfur atoms wherein the pigments in the CGL layers are either vacuum evaporated or dispersed in binder resins and a layer of tetraaryl biphenyl hole transporting molecules.

U.S. Pat. No. 4,517,270 illustrates bisimides with propyl, hydroxypropyl, methoxypropyl and phenethyl substituents (3a, R=CH$_3$CH$_2$CH$_2$—, HOCH$_2$CH$_2$CH$_2$—, CH$_3$OCH$_2$CH$_2$ CH$_2$—, and C$_6$H$_5$CH$_2$CH$_2$—) which are black or dark primarily because of their crystal properties, and perylene pigments which are nuclearly substituted with anilino, phenylthio, or p-phenylazoanilino groups. Pigments of this type were indicated as providing good electrophotographic recording media with panchromatic absorption characteristics. Similarly, in U.S. Pat. No. 4,719,163 and U.S. Pat. No. 4,746,741 the pigment N,N'-bis(2-(3-methylphenyl)ethyl)perylene-3,4,9,10-bis(dicarboximide) (3a, R=3-methyl-C$_6$H$_5$CH$_2$CH$_2$—) is indicated as providing layered electrophotographic devices having spectral response to beyond 675 nanometers.

Two additional patents relating to the use of perylene pigments in layered photoreceptors are U.S. Pat. No. 5,019,473, which illustrates a grinding process to provide finely and uniformly dispersed perylene pigment in a polymeric binder with excellent photographic speed, and U.S. Pat. No. 5,225,307, the disclosure of which is totally incorporated herein by reference, which discloses a vacuum sublimation process which provides a photoreceptor pigment, such as bis(benzimidazo)perylene (3b, X=1,2-phenylene) with superior electrophotographic performance.

The following patents relate to the use of perylene compounds, either as dissolved dyes or as dispersions in single layer electrophotographic photoreceptors usually based on sensitized poly(vinyl carbazole) compositions: U.S. Pat. Nos. 4,469,769; 4,514,482; 4,556,622; Japanese JP 84-31,957, -119,356, -119,357, -140,454, -140,456, -157,646, -157,646, and -157,651.

While the above described layered perylene-based photoreceptors, or photoconductive imaging members may exhibit desirable xerographic electrical characteristics, most of the bisimides are red to brown in color, and possess, it is believed, relatively poor spectral response, particularly to the 600 to 700 nanometers region of the spectrum. The majority of the bis(imidazo) pigments, especially those with a purple to violet color, have poor spectral response in the blue (400 to 450 nanometers) region of the spectrum. Ideally, a photoconductive pigment used for light lens imaging, particularly for color photocopying, should have a uniform spectral response, that is, be panchromatic throughout the visible spectrum from about 400 to about 700 nanometers.

Although a number of known imaging members are suitable for their intended purposes, a need remains for imaging members containing improved photogenerator pigments. In addition, a need exists for imaging members containing photoconductive components with improved xerographic electrical performance including higher charge acceptance, lower dark decay, increased charge generation efficiency and charge injection into the transporting layer, tailored PIDC curve shapes to enable a variety of reprographic applications, reduced residual charge and/or reduced erase energy, improved long term cycling performance, and less variability in performance with environmental changes in temperature and relative humidity. There is also a need for imaging members with photoconductive components comprised of certain photogenerating pigments with enhanced dispersability in polymers and solvents. There is also a need for photogenerating pigments which permit the preparation of coating dispersions, particularly in dip-coating operations, which are colloidally stable and wherein settlement is avoided or minimized, for example little settling for a period of from 20 to 30 days in the absence of stirring. Further, there is a need for photoconductive materials with enhanced dispersability in polymers and solvents that enable low cost coating processes in the manufacture of photoconductive imaging members. Additionally, there is a need for photoconductive materials that enable imaging members with enhanced photosensitivity in the red region of the light spectrum, enabling the resulting imaging members thereof to be selected for imaging by red diode and gas lasers. Furthermore, there is a need for photogenerator pigments with spectral response in the green and blue regions of the spectrum to enable imaging by newly emerging blue and green electronic imaging light sources. A need also exists for improved panchromatic pigments with broad spectral response from about 400 to 700 nanometers for color copying using light-lens processes. There also is a need for photogenerating pigments which can be readily prepared from commercially available reactants, and for preparative processes and purification techniques which provide highly pure pigment with outstanding xerographic electrical performance, without recourse to expensive and time consuming post-synthetic purification methods such as solvent extraction or vacuum sublimation. These and other needs may be accomplished, it is believed, in embodiments of the present invention

SUMMARY OF THE INVENTION

Examples of objects of the present invention include:

It is an object of the present invention to provide unsymmetrical perylene bisimide dimers and imaging members thereof with many of the advantages illustrated herein.

It is another object of the present invention to provide imaging members with novel photoconductive components with improved photoconductivity.

Additionally in another object of the present invention there are provided (1) unsymmetrical perylene bisimide dimers suitable for use as dispersed colorants in polymeric composites and as photogenerator pigments in layered photoconductive imaging devices; (2) unsymmetrical perylene bisimide dimers comprised of two perylene bisimide moieties joined together by an unsymmetrical bridging group; processes for the preparation of dimeric pigments from readily available starting materials; and processes for the purification of these dimers which enable photoelectrically stable materials for their selection as photogenerator pigments in photoconductive imaging devices, or members; and wherein two perylene moieties are linked together by imide nitrogens.

It is another object of the present invention to provide photoconductive imaging members with unsymmetrical perylene dimer photogenerating pigments with the formulas illustrated herein, and that enable imaging members with improved photosensitivity in the visible wavelength region of light spectrum, such as from about 400 to about 700 nanometers.

It is another object of the present invention to provide unsymmetrical dimeric pigments which can possess a variety of colors such as magenta, red, brown, black, green, and the like; the color being primarily dependent on the types of terminal and bridging groups present.

Still, another object of the present invention relates to the provision of novel compounds, and more specifically, compounds of the formulas illustrated herein.

Another object of the present invention relates to the preparation of unsymmetrical perylene dimer photogenerating pigments having structures illustrated in Formula 1.

Embodiments of the present invention relate to the provision of layered imaging members comprised of a supporting substrate, a photogenerating layer comprised of photogenerating pigments comprised of unsymmetrical perylene bisimide dimers, such as those of Formula 1, and more specifically, wherein R is hydrogen, alkyl, such as methyl, ethyl, n-propyl, n-butyl, isobutyl, n-pentyl, 2-methylbutyl, 3-methylbutyl, n-hexyl, phenyl, benzyl, phenethyl and the like, and X-Y is an unsymmetrical bridging group such as alkylene, arylene, aralkylene, and the like.

Unsymmetrical alkylenes, representative formulas of which are illustrated hereinafter, include 1,2-propylene, 1-methyl-1,3-propylene, 1-ethyl-1,3-propylene, 1-methyl-1,4-tetramethylene, 2-methyl-1,4-tetramethylene, 1-methyl-1,5-pentamethylene, 2-methyl-1,5-pentamethylene and higher unsymmetric alkylene groups with up to about 20 carbon atoms. Unsymmetric substituted alkylenes include, for example, 3-hydroxy-1,2-propylene, 2-hydroxy-1,4-tetramethylene, 2-methoxy-1,4-tetramethylene, 2-carboxy-1,4-tetramethylene and 2-dimethylamino-1,4-tetramethylene. Arylene refers, for example, to unsymmetrically substituted bridging groups such as 2,4-, 2,3'-, 2,4'-, and 3,4'-biphenylene, and 1,3-, 1,6- and 1,7-naphthylene. Substituted arylenes refers, for example, to groups such as 2-chloro-1,4-phenylene, 2-methyl-4,4'-biphenylene, N-phenylbenzamide-3,4'-diyl, diphenylsulfone-3,4'-diyl and diphenylether-3,4'-diyl. Aralkylene includes benzyl-, phenethyl-, phenylpropyl- and fluorenyl- groups in which one perylene bisimide moiety is bonded to the alkyl group and the second is bonded to the 2-, 3- or 4- position of the aromatic ring. Substituted aralkylene refers, for example, to groups of the aforementioned class in which substituents such as methyl, tertiary-butyl, halogen of, for example, fluoro, chloro, bromo, and iodo, hydroxy, methoxy, nitro, cyano and dimethylamino are attached to the aromatic ring.

In embodiments, the imaging members of the present invention are comprised of, preferably in the order indicated, a conductive substrate, a photogenerating layer comprising unsymmetrical perylene bisimide dimer pigments dispersed in a resinous binder composition, and a charge transport layer, which comprises charge transporting molecules dispersed in an inactive resinous binder composition.

In embodiments, the photoconductive imaging member comprises a conductive substrate, a hole transport layer comprising a hole transport composition, such as an aryl amine, dispersed in an inactive resinous binder composition, and as a top layer a photogenerating layer comprised of unsymmetrical perylene bisimide dimer pigments optionally dispersed in a resinous binder composition; or a conductive substrate, a hole blocking metal oxide layer, an optional adhesive layer, a photogenerating layer comprised of the unsymmetrical perylene bisimide dimer pigment of the present invention, optionally dispersed in a resinous binder composition, and an aryl amine hole transport layer comprising aryl amine hole transport molecules optionally dispersed in a resinous binder.

Specific examples of unsymmetrical perylene dimer pigments of the present invention and encompassed by the Formula 1 illustrated herein include those wherein R is hydrogen, methyl, ethyl, n-propyl, isopropyl, 3-methoxypropyl, 3-hydroxypropyl, cyclopropyl, cyclopropylmethyl, n-butyl, isobutyl, secbutyl, cyclobutyl, n-pentyl, 2-pentyl, 3-pentyl, 2-(3-methyl)butyl, 2-methylbutyl, 3-methylbutyl, neopentyl, cyclopentyl, n-hexyl, 2-ethylhexyl, cyclohexyl, n-heptyl, cycloheptyl, n-octyl, cyclooctyl, n-nonyl, n-decyl, n-undecyl, n-dodecyl, cyclododecyl, phenyl, benzyl, phenethyl and substituted phenyl, benzyl and phenethyl radicals in which the aromatic ring contains from 1 to 5 substituents inclusive of fluorine, chlorine, bromine, iodine, methyl, hydroxymethyl, trifluoromethyl, tertiary-butyl, tertiary-butoxy, methoxy, trifluoromethoxy, nitro, cyano, dimethylamino, diethylamino, and the like and X-Y represents an unsymmetrical bridging group inclusive of, but not limited to, the following specific examples.

X–Y = Unsymmetrical Alkylene $$\begin{array}{ccc}
\text{CH}_3 & \text{CH}_2\text{CH}_3 & \text{CH}_3 \\
| & | & | \\
-\text{CH}_2\text{CH}- & -\text{CH}_2\text{CH}- & -\text{CH}_2\text{CH}_2\text{CH}-
\end{array}$$

$$\begin{array}{ccc}
\text{CH}_2\text{CH}_3 & \text{CH}_3 & \text{CH}_3 \\
| & | & | \\
-\text{CH}_2\text{CH}_2\text{CH}- & -\text{CH}_2\text{CH}_2\text{CH}- & -\text{CH}_2\text{CH}_2\text{CHCH}_2-
\end{array}$$

$$\begin{array}{cc}
\text{CH}_3 & \text{CH}_3 \\
| & | \\
-\text{CH}_2\text{CH}_2\text{CH}_2\text{CH}- & -\text{CH}_2\text{CH}_2\text{CH}_2\text{CHCH}_2-
\end{array}$$

-continued

X–Y = Unsymmetrical Substituted Alkylene $$\begin{array}{ccc}
\text{OCH}_3 & \text{OH} & \text{N(CH}_3)_2 \\
| & | & | \\
-\text{CH}_2\text{CH}_2\text{CHCH}_2- & -\text{CH}_2\text{CH}_2\text{CHCH}_2- & -\text{CH}_2\text{CH}_2\text{CHCH}_2-
\end{array}$$

X–Y = Arylene

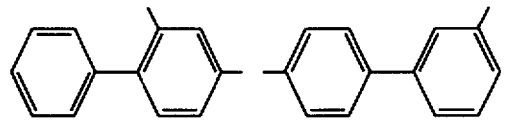

X–Y = Substituted Arylene

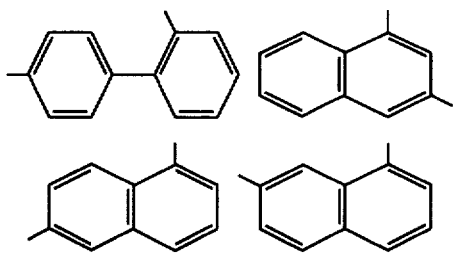

X = F, Cl, Br, OH, CH$_3$, OCH$_3$, (CH$_3$)$_2$N, CN, NO$_2$, etc.

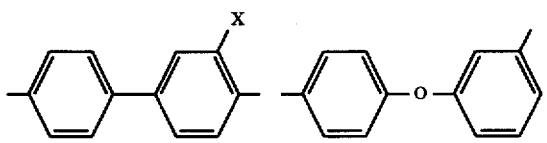

Examples of Unsymmetrical X-Y Bridging Groups

X–Y = Aralkylene

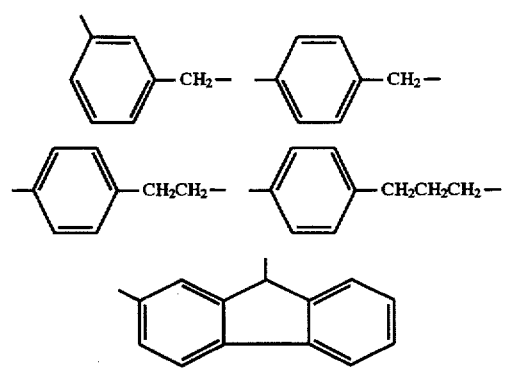

-continued

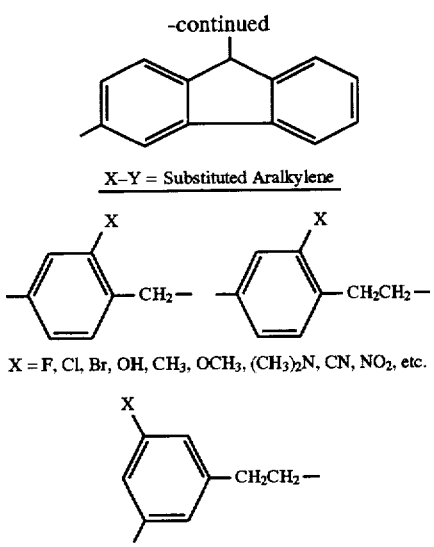

X—Y = Substituted Aralkylene

X = F, Cl, Br, OH, CH$_3$, OCH$_3$, (CH$_3$)$_2$N, CN, NO$_2$, etc.

Specific examples of photogenerating unsymmetric perylene bisimide dimers of the present invention include those encompassed by Formula 1 wherein R is hydrogen, methyl, ethyl, n-propyl, allyl, 3-methoxypropyl, n-butyl, isobutyl, n-pentyl, 2-methylbutyl, 3-methylbutyl, neopentyl, n-hexyl, n-heptyl, n-octyl, phenyl, benzyl, 3-chlorobenzyl and phenethyl, and X-Y is propane-1,2-diyl, butane-1,2-diyl, butane-1,3-diyl, 2-methylbutane-1,4-diyl, pentane-1,3-diyl, pentane-1,4-diyl, 2-methylpentane-1,5-diyl, toluene-a,4-diyl, ethylbenzene-b,4-diyl and diphenyl ether-3',4'-diyl.

The substrate can be formulated entirely of an electrically conductive material, or it can be comprised of an insulating material having an electrically conductive surface. The substrate can be of an effective thickness, generally up to about 100 mils, and preferably from about 1 to about 50 mils, although the thickness can be outside of this range. The thickness of the substrate layer depends on many factors, including economic and mechanical considerations. Thus, this layer may be of substantial thickness, for example over 100 mils, or of minimal thickness provided that there are no adverse effects thereof. In a particularly preferred embodiment, the thickness of this layer is from about 3 mils to about 10 mils. The substrate can be opaque or substantially transparent and can comprise numerous suitable materials having the desired mechanical properties. The entire substrate can comprise the same material as that in the electrically conductive surface, or the electrically conductive surface can merely be a coating on the substrate. Any suitable electrically conductive material can be employed. Typical electrically conductive materials include copper, brass, nickel, zinc, chromium, stainless steel, conductive plastics and rubbers, aluminum, semitransparent aluminum, steel, cadmium, titanium, silver, gold, paper rendered conductive by the inclusion of a suitable material therein or through conditioning in a humid atmosphere to ensure the presence of sufficient water content to render the material conductive, indium, tin, metal oxides, including tin oxide and indium tin oxide, and the like. The substrate layer can vary in thickness over substantially wide ranges depending on the desired use of the electrophotoconductive member. Generally, the conductive layer ranges in thickness of from about 50 Angstroms to many centimeters, although the thickness can be outside of this range. When a flexible electrophotographic imaging member is desired, the thickness typically is from about 100 Angstroms to about 750 Angstroms. The substrate can be of any other conventional material, including organic and inorganic materials. Typical substrate materials include insulating nonconducting materials such as various resins known for this purpose including polycarbonates, polyamides, polyurethanes, paper, glass, plastic, polyesters such as MYLAR® (available from E.I. DuPont) or MELINEX 447® (available from ICI Americas, Inc.), and the like. If desired, a conductive substrate can be coated onto an insulating material. In addition, the substrate can comprise a metallized plastic, such as titanized or aluminized MYLAR®, wherein the metallized surface is in contact with the photogenerating layer or any other layer situated between the substrate and the photogenerating layer. The coated or uncoated substrate can be flexible or rigid, and can have any number of configurations, such as a plate, a cylindrical drum, a scroll, an endless flexible belt, or the like. The outer surface of the substrate preferably comprises a metal oxide such as aluminum oxide, nickel oxide, titanium oxide, and the like.

In embodiments, intermediate adhesive layers between the substrate and subsequently applied layers may be desirable to improve adhesion. When such adhesive layers are utilized, they preferably have a dry thickness of from about 0.1 micron to about 5 microns, although the thickness can be outside of this range. Typical adhesive layers include film-forming polymers such as polyester, polyvinylbutyral, polyvinylpyrrolidone, polycarbonate, polyurethane, polymethylmethacrylate, and the like as well as mixtures thereof. Since the surface of the substrate can be a metal oxide layer or an adhesive layer, the expression substrate is intended to also include a metal oxide layer with or without an adhesive layer on a metal oxide layer. Moreover other known layers may be selected for the photoconductive imaging members of the present invention, such as polymer protective overcoats, and the like.

The photogenerating layer is of an effective thickness, for example, of from about 0.05 micron to about 10 microns or more, and in embodiments has a thickness of from about 0.1 micron to about 3 microns. The thickness of this layer can be dependent primarily upon the concentration of photogenerating material in the layer, which may generally vary from about 5 to 100 percent. The 100 percent value generally occurs when the photogenerating layer is prepared by vacuum evaporation of the pigment. When the photogenerating material is present in a binder material, the binder contains, for example, from about 25 to about 95 percent by weight of the photogenerating material, and preferably contains about 60 to 80 percent by weight of the photogenerating material. Generally, it is desirable to provide this layer in a thickness sufficient to absorb about 90 to about 95 percent or more of the incident radiation which is directed upon it in the imagewise or printing exposure step. The maximum thickness of this layer is dependent primarily upon factors such as mechanical considerations, such as the specific photogenerating compound selected, the thicknesses of the other layers, and whether a flexible photoconductive imaging member is desired.

Typical transport layers are described, for example, in U.S. Pat. Nos. 4,265,990; 4,609,605; 4,297,424 and 4,921,773, the disclosures of each of these patents being totally incorporated herein by reference. Organic charge transport materials can also be employed.

Hole transport molecules of the type described in U.S. Pat. Nos. 4,306,008; 4,304,829; 4,233,384; 4,115,116; 4,299,897; 4,081,274, and 5,139,910, the disclosures of each are totally incorporated herein by reference, can be selected for the imaging members of the present invention. Typical diamine hole transport molecules include N,N'-diphenyl-N, N'-bis(3-methylphenyl)-(1,1'-diphenyl)-4,4'-diamine, N,N'-diphenyl-N,N'-bis(4-methylphenyl)-(1,1'-biphenyl)-4,4'-diamine, N,N'-diphenyl-N,N'-bis(2-methylphenyl)-(1 ,1'-biphenyl)-4,4'-diamine, N,N'-diphenyl-N,N'-bis(3-ethylphenyl)-(1,1'-biphenyl)-4,4'-diamine, N,N'-diphenyl-N, N'-bis(4-ethylphenyl)-(1,1'-biphenyl)-4,4'-diamine, N,N'-diphenyl-N,N'-bis(4-n-butylphenyl)-(1,1'-biphenyl)-4, 4'-diamine, N,N'-diphenyl-N,N'-bis(3-chlorophenyl)-(1,1'-biphenyl)-4,4'-diamine, N,N'-diphenyl-N,N'-bis(4-chlorophenyl)-(1,1'-biphenyl)-4,4'-diamine, N,N'-diphenyl-N,N'-bis(phenylmethyl)-(1,1'-biphenyl)-4,4'-diamine, N,N, N', N'-tetraphenyl-[2,2'-dimethyl-1,1'-biphenyl]-4,4'-diamine, N,N,N',N'-tetra-(4-methylphenyl)-[2,2'-5 dimethyl-1,1'-biphenyl]-4,4'-diamine, N,N'-diphenyl-N,N'-bis(4-methylphenyl)-[2,2'-dimethyl-1,1'-biphenyl]-4,4'-diamine, N,N'-diphenyl-N,N'-bis(2-methylphenyl)-[2,2'-dimethyl-1,1'-biphenyl]-4,4'-diamine, N,N'-diphenyl-N,N'-bis(3-methylphenyl)-[2,2'-dimethyl-,1,1'-biphenyl]-4,4'-diamine, N, N'-diphenyl-N,N'-bis(3-methylphenyl)-pyrenyl-1,6-diamine, and the like.

In embodiments of the present invention, the preferred hole transport layer, since it enables excellent effective transport of charges, is comprised of aryldiamine components as represented, or essentially represented, by the general formula of, for example, the U.S. patents indicated herein, such as U.S. Pat. No. 4,265,990, wherein X, Y and Z are selected from the group consisting of hydrogen, an alkyl group with, for example, from 1 to about 25 carbon atoms and a halogen, preferably chlorine, and at least one of X, Y and Z is independently an alkyl group or chlorine. When Y and Z are hydrogen, the compound may be N,N'-diphenyl-N,N'-bis(alky(phenyl)-(1,1'-biphenyl)-4,4'-diamine wherein alkyl is, for example, methyl, ethyl, propyl, n-butyl, or the like, or the compound may be N,N'-diphenyl-N,N'-bis(chlorophenyl)-(1,1'-biphenyl)-4,4'-diamine.

The charge transport component is present in the charge transport layer in an effective amount, generally from about 5 to about 90 percent by weight, preferably from about 20 to about 75 percent by weight, and more preferably from about 30 to about 60 percent by weight, although the amount can be outside of this range.

Examples of the highly insulating and transparent resinous components or inactive binder resinous material for the transport layer include binders such as those described in U.S. Pat. No. 3,121,006, the disclosure of which is totally incorporated herein by reference. Specific examples of suitable organic resinous materials include polycarbonates, acrylate polymers, vinyl polymers, cellulose polymers, polyesters, polysiloxanes, polyamides, polyurethanes, polystyrenes, and epoxies as well as block, random or alternating copolymers thereof. Preferred electrically inactive binder materials are polyearbonate resins having a molecular weight of from about 20,000 to about 100,000 with a molecular weight in the range of from about 50,000 to about 100,000 being particularly preferred. Generally, the resinous binder contains from about 5 to about 90 percent by weight of the active material corresponding to the foregoing formula, and preferably from about 20 percent to about 75 percent of this material.

Similar binder materials may be selected for the photogenerating layer, including polyesters, polyvinyl butyrals, polyvinylcarbazole, polycarbonates, polyvinyl formals, poly (vinylacetals) and those illustrated in U.S. Pat. No. 3,121, 006, the disclosure of which is totally incorporated herein by reference.

The photoconductive imaging member may optionally contain a charge blocking layer situated between the conductive substrate and the photogenerating layer. This layer may comprise metal oxides, such as aluminum oxide and the like, or materials such as silanes and nylons. Additional examples of suitable materials include polyisobutyl methacrylate, copolymers of styrene and acrylates such as styrene/n-butyl methacrylate, copolymers of styrene and vinyl toluene, polycarbonates, alkyl substituted polystyrenes, styrene-olefin copolymers, polyesters, polyurethanes, polyterpenes, silicone elastomers, mixtures thereof, copolymers thereof, and the like. The primary purpose of this layer is to prevent charge injection from the substrate during and after charging. This layer is of a thickness of less than 50 Angstroms to about 10 microns, preferably being no more than about 2 microns.

In addition, the photoconductive imaging member may also optionally contain an adhesive interface layer situated between the hole blocking layer and the photogenerating layer. This layer may comprise a polymeric material such as polyester, polyvinyl butyral, polyvinyl pyrrolidone and the like. Typically, this layer is of a thickness of less than about 0.6 micron.

The unsymmetrical dimers of the present invention can be readily prepared by reaction, or condensation of about 2 to about 5 equivalents of a perylene monoimide-monoanhydride as illustrated in Formula 2, with one equivalent of an unsymmetrical diamine such as 1,2-diaminopropane, 2-methyl-1,5-diaminopentane, 4-aminobenzylamine, 4-aminophenethylamine, 3,4'-diaminodiphenyl ether, 4,4'-diaminobenzanilide or 3,4'-diaminodiphenylsulfone in an organic solvent, such as chloronaphthalene, trichlorobenzene, decalin, tetralin, aniline, dimethylformamide, dimethylsulfoxide, N-methylpyrrolidone and the like with the optional use of appropriate catalysts, such as zinc acetate or zinc iodide, in an amount equivalent to about 1 to 50 mole percent of the perylene. The concentration of reactants in the solvent can range from about 50 weight percent combined diamine and anhydride, and 50 percent solvent to about 2 percent diamine and anhydride, and 98 percent solvent with a preferred range being from about 5 percent diamine and anhydride and 95 percent solvent to 20 percent diamine and anhydride and 80 percent solvent. The reactants are stirred in the solvent and heated to a temperature of from about 100° C. to 300° C., and preferably from 150° C. to 205° C. for a period of from 10 minutes to about 8 hours depending on the rate of the reaction. The mixture is subsequently cooled to a temperature of between about 25° C. to about 175° C., and the solid pigment perylene product is separated from the mother liquors by filtration through, for example, a fine porosity sintered glass filter funnel or a glass fiber filter. The pigment product is then subjected to a number of washing steps using hot and cold solvents such as dimethyl formamide, methanol, water and alcohols. Optionally, the pigment may be washed with dilute hot or cold aqueous base solution such as 5 percent of sodium hydroxide or potassium carbonate which serves to remove by conversion to a water soluble salt any residual starting anhydride and other acidic contaminants. Also, optionally the unsymmetrical dimeric perylene pigment product may also be washed with dilute acid such as 2 percent aqueous hydrochloric acid which serves to remove residual metal salts, such as for example zinc acetate which can be optionally used as a reaction catalyst. Finally, the pigment is dried either at ambient temperature or at temperatures up to 200° C. at atmospheric pressure or under vacuum. The yield of product, referred to as "as-synthesized pigment", ranges from about 50 percent to nearly 100 percent.

More specifically, the process of the present invention comprises stirring a mixture of 2.2 molar equivalents of a perylene tetracarboxylic acid mono imide-mono anhydride having the structure of Formula 2 with R=n-propyl, n-phenyl and the like in N-methylpyrrolidinone solvent in an amount corresponding to about 50 parts by weight of solvent to about 2 parts of monoanhydride at room temperature, followed by adding 1 molar equivalent of an unsymmetric diamine, such as 2-methyl-1,5-diaminopentane or 4-aminobenzylamine and, optionally, a catalyst known to speed up the reaction of amine with anhydrides, such as zinc acetate dihydrate, in an amount corresponding to about 0.5 equivalents, to this mixture. Stirring this mixture and heating until the solvent begins to reflux (N-methylpyrrolodinone boils at 202° C.) during which treatment the diamine reacts sequentially with two molecules of the monoanhydride to form the dimeric perylene pigment molecule. Maintaining the heating and stirring at the solvent reflux temperature for a period of about 2 hours ensures completion of the reaction. Thereafter, cooling the reaction mixture to about 150° C. and filtering the mixture through a filter such as fine-porosity sintered glass of a glass-fiber filter which has been preheated to about 150° C. with, for example, boiling solvent such as dimethylformamide (DMF). Washing the pigment in the filter with DMF heated to about 150° C. (which serves to dissolve and thus remove any residual starting anhydride) until the color of the filtrate wash becomes, and remains, colorless or light orange was then accomplished. The pigment is then washed with DMF at room temperature, about 25° C., and is finally washed with acetone, methanol or a similar low-boiling solvent and is dried at 60° C. in an oven.

Optionally, water can be used in the final washing step and the pigment wet cake can be freeze dried. This process generally provides free-flowing pigment which is more readily redispersed in solvent than solvent washed pigment which has been dried using other methods which can sometimes result in the formation of a hard, caked mass of pigment which is difficult to redisperse.

Also optionally, in situations where the hot, for example 60° to 150° C., solvent, for example DMF, fails to completely remove all the excess starting monoanhydride from the dimer the product can be dispersed in dilute, for example 1 to 5 percent of aqueous potassium hydroxide for a period of time of from about 1 hour to about 24 hours, and preferably from about 7 to about 20 hours, at room temperature, about 25° C. to about 90° C., which treatment converts the monoimide to a water-soluble, deep purple-colored dipotassium carboxylate salt, followed by filtration and washing the solid with water until the filtrate becomes colorless. The residual starting anhydride in the product can be detected by known spectroscopic methods such as FT-IR and NMR, or by a color spot test in which the product is stirred in dilute, for example about 2 percent of aqueous potassium hydroxide solution with the presence of monoanhydride being indicated by the development of a deep reddish purple color characteristic of the dipotassium salt of the monoimide.

Also optionally, in situations where a metal-containing catalyst, such as zinc acetate dihydrate, has been used to improve the reaction rate the product can be stirred in a dilute acid, such as 2 percent aqueous hydrochloric acid, which process coverts the residual metal to water soluble salts, which can then be removed by filtration and washing with water.

The unsymmetrical photogenerating compounds of the present invention in embodiments thereof enable enhanced photosensitivity in the visible wavelength range. In particular, imaging members with photosensitivity at wavelengths of from about 400 to 700 nanometers are provided in embodiments of the present invention, which renders them particularly useful for color copying and imaging and printing applications, such as red LED and diode laser printing processes, which typically require sensitivity from about 600 to about 700 nanometers.

The present invention also encompasses a method of generating images with the photoconductive imaging members disclosed herein. The method comprises the steps of generating an electrostatic latent image on a photoconductive imaging member of the present invention, developing the latent image with a toner comprised of resin, pigment like carbon black, and a charge additive, and transferring the developed electrostatic image to a substrate. Optionally, the transferred image can be permanently affixed to the substrate. Development of the image may be achieved by a number of methods, such as cascade, touchdown, powder cloud, magnetic brush, and the like. Transfer of the developed image to a substrate, such as paper, may be by any method, including those making use of a corotron or a biased roll. The fixing step may be performed by means of any suitable method, such as flash fusing, heat fusing, pressure fusing, vapor fusing, and the like. Any substrate selected for xerographic copiers and printers, including digital copiers, may be used as a substrate, such as paper, transparency material, and the like.

Specific embodiments of the invention will now be described in detail. These Examples are intended to be illustrative, and the invention is not limited to the materials, conditions, or process parameters set forth in these embodiments. All parts and percentages are by weight unless otherwise indicated.

SYNTHESIS EXAMPLES

The starting monoanhydride monoimides in the following Examples were prepared by the methods described in U.S. Pat. No. 4,501,906, the disclosure of which is totally incorporated herein by reference, (Hoechst) or by minor adaptations of the processes described therein. The structures of the product dimers described below were mainly established by $^1$H and $^{13}$C nuclear magnetic resonance spectrometry in trifluoroacetic acid-containing solvent mixtures. Visible absorption spectra in trifluoroacetic acid-methylene chloride solution were also measured for each product. The bisimide dimers evidence absorbance maxima at about 500 and 540 nanometers which is diagnostic for the perylene bisimide chromophore in this solvent system. Trivial names, based on the substituent groups and referring to the perylene bisimide moiety as the imidoperyleneimido group have been used. To avoid or minimize confusion and ambiguity, the compounds are also described in relation to the structures shown in Formula 1.

The synthesis Examples that follow are representative of the general synthesis and purification processes selected.

Synthesis Example 1

Preparation of 1,5-Bis(n-butylimidoperyleneimido)-2-methylpentane (Formula 1, R and R=n-butyl, X-Y=2-methyl-1,5-pentamethylene):

A suspension of mono-n-butylimidoperylene monoanhydride (Formula 2, R=n-butyl; 2.46 grams, 0.0055 mole) in 100 milliliters of N-methylpyrrollidinone (NMP) was treated with 0.2905 gram (0.338 milliliter, 0.00250 mole) of 1,5-diamino-2-methylpentane (Dytek A). The resulting mixture was then stirred and was heated to reflux (202° C.) for 2½ hours. The resultant thick dark brown reaction mixture was cooled to 150° C. then was filtered through a 9 centimeter glass fiber filter, Whatman Grade 934AH, which had been preheated by pouring 100 milliliters of boiling dimethylformamide (DMF) solvent (boiling point 150° C.) through it. The resulting solid product was washed in the funnel with 3×75 milliliters portions of boiling DMF. The final wash filtrate was a faint pink color. The solid was washed with 25 milliliters of cold DMF then with 2×25 milliliters of methanol and was dried at 60° C. to provide 2.25 grams (92 percent yield) of dark chocolate brown solid product.

A spot test for the presence of starting monoanhydride which was accomplished by stirring about 50 milligrams of the above product pigment in 2 milliliters of 2 percent aqueous potassium hydroxide solution for 4 hours at room temperature, about 25° C. was negative, there being no sign of the deep red-purple color characteristic of the monoimide dicarboxylate salt.

Synthesis Example 2
Preparation of 1,5-Bis(n-pentylimidoperyleneimido)-2-methylpentane (Formula 1, R and R=n-pentyl, X-Y=2-methyl-1,5-pentamethylene):

A mixture of 2.54 grams (0.0055 mole) of mono-n-pentylimidoperylene monoanhydride (Formula 2, R=n-pentyl) and Dytek A diamine (0.338 milliliter, 0.00250 mole) in 100 milliliters of NMP was stirred and heated at reflux (202° C.) for 2.74 hours, then was cooled to 150° C. The solid product resulting was hot filtered and washed with boiling DMF, cold DMF and methanol as in the above Example 1. Drying at 60° C. for 16 hours provided 2.20 grams (88 percent yield) of a brownish red solid product. A spot test for the presence of starting monoimide was negative.

Synthesis Example 3
Preparation of Bis-1,3-(n-propylimidoperyleneimido)-1-ethylpropane (Formula 1, R and R=n-propyl, X-Y=1-ethyl-1,3-propylene):

A suspension of 4.76 grams (0.011 mole) of monopropylimidoperylene monoanhydride (Formula 2, R=n-propyl) in 300 milliliters of NMP was treated with 0.511 gram ( 0.598 milliliters, 0.005 mole) of 1,3-diaminopentane (Dytek EP). The resulting mixture was stirred at room temperature, about 25° C. throughout, for 15 minutes, then was heated at reflux for 2½ hours. The resultant dark reddish brown solution was cooled to room temperature and was filtered. The solid product was washed with DMF until the filtrate became a light orange color. The solid was washed with 2×20 milliliters of methanol and then was dried at 600° C. to provide 2.6 grams of a brown solid product of bis-1,3-(n-propylimidoperyleneimido)-1-ethylpropane (Formula 1, R=n-propyl, X-Y=1-ethyl-1,3-propylene).

When a sample, about 10 grams, of the above obtained product was stirred in a 2 percent aqueous solution of potassium hydroxide, a reddish purple color developed which is indicative of residual starting anhydride in the product. The product was stirred in 200 milliliters of water containing 4 grams of potassium hydroxide for 5 hours at about 60° C., the resultant suspension was filtered, and the solid product was washed with 5×100 milliliters of water until the filtrate changed from reddish purple to colorless. The solid was then dried at 60° C. to provide 1.3 gram (28 percent yield) of the above dark brown solid product.

Synthesis Example 4
Preparation of a-4-Bis(n-butylimidoperyleneimido) methylbenzene (Formula 1, R and R=n-butyl, X-Y=a-4-tolyl):

A mixture of n-butylimidoperylene monoanhydride (Formula 2, R=n-butyl; 2.46 grams, 0.0055 mole) and 4-aminobenzylamine (0.305 gram, 0.00250 mole) and zinc acetate dihydrate (0.44 gram, 0.0020 mole) in 100 milliliters of NMP was stirred at room temperature, about 25° C., for 30 minutes. The resulting mixture was then heated at reflux for 45 minutes, was cooled to 155° C., and was then filtered through a preheated glass fiber filter. The solid product was washed with 4×30 milliliters portions of boiling DMF, then with 20 milliliters of cold DMF and 2×20 milliliters portions of methanol. Drying at 60° C. provided 2.20 grams of a black solid product of a-4-bis(n-butylimidoperyleneimido) methylbenzene (Formula 1, R=n-butyl, X-Y=a-4-tolyl), (91 percent yield). A spot test for the presence of starting monoanhydride was negative.

Synthesis Example 5
Preparation of b-4-Bis(n-pentylimidoperyleneimido) ethylbenzene (Formula 1, R and R=n-pentyl, X-Y=b-4-ethylbenzene):

A mixture of n-pentylimidoperylene monoanhydride (Formula 2, R=n-pentyl; 2.54 grams, 0.0055 mole), b-(4-amino)phenethylamine (0.341 gram, 0.329 milliliter, 0.00250 mole) and zinc acetate dihydrate (0.55 gram, 0.0025 mole) in 100 milliliters of NMP was stirred at room temperature for 30 minutes, followed by heating at reflux for 1.75 hours. The resultant reddish brown suspension was cooled to 150° C., filtered and washed as in Example 4. Drying at 60° C. provided 2.3 grams (90 percent) of the above reddish brown solid product of b-4-bis(n-pentylimidoperyleneimido)ethylbenzene (Formula 1, R=n-pentyl, X-Y=b-4-ethylbenzene). A spot test for starting monoanhydride reactant was negative.

Synthesis Example 6
Preparation of 4,4'-Bis(n-propylimidoperyleneimido) benzanilide (Formula 1, R and R=n-propyl, X-Y= benzanilide-4,4'-diyl):

Propylimidoperylene monoanhydride (4.76 grams, 0.011 mole), 4,4'-diaminobenzanilide (1.135 grams, 0.0050 mole) and zinc acetate dihydrate (1.1 grams, 0 0050 mole) were stirred and heated to reflux in 200 milliliters of NMP. After 2.33 hours, the mixture was cooled to 150° C. and was filtered through an 11 centimeter glass fiber filter (Whatman Grade GF/F) which had been preheated with 50 milliliters of boiling DMF. The solid product was washed in the funnel with 5×50 milliliter portions of boiling DMF then with 50 milliliters of cold DMF, and 2×25 milliliters of water. The resulting wet cake was stirred in 300 milliliters of 3 percent aqueous hydrochloric acid for 2 hours at 60° C. The resultant dispersion was filtered and the solid product was washed with 4×100 milliliter portions of water, then was dried at 60° C. to provide 3.9 grams (74 percent) of the above orange solid product. A spot test indicated that there was no residual starting monoimide in this product.

Synthesis Example 7
Preparation of 3,4'-Bis(n-pentylimidoperyleneimido) diphenyl ether (Formula 1, R and R=n-pentyl, X-Y= diphenyl ether-3,4"-diyl):

A mixture of n-pentylimidoperylene monoanhydride (Formula 2, R=n-Pentyl; 5.07 grams, 0.011 mole), 3,4'-diaminophenyl ether (1.00 gram, 0.0050 mole) and zinc acetate dihydrate (1.1 grams, 0.005 mole) in 200 milliliters of NMP was stirred and heated to reflux under argon. After 3.33 hours at reflux the dark brown reaction mixture was cooled to 160° C., was filtered and washed with boiling DMF then water and then treated with 3 percent aqueous hydrochloric acid in the same manner as Example 6. The product resulting above was dried at 60° C. to provide 4.9 grams (90 percent) to provide as a dull red powder.

Comparative Synthesis Example 1

A Monomeric Perylene Bisimide

Preparation of N,N'-Bis(n-pentyl)perylene-3,4,9,10-tetracarboxylic diimide (Formula 3a, Both Rs=n-pentyl):

A mixture of 3,4,9,10-perylenetetracarboxylic dianhydride (3.92 grams, 0.010 mole) and n-pentylamine (4.5 grams, 0.060 mole) in 200 milliliters of NMP was stirred and heated to reflux. After ½ hour at reflux the resulting dark brown solution was cooled to 150° C. and the suspension was filtered through a preheated sintered glass funnel. The solid product resulting was washed in the funnel with 3×100 milliliters of boiling DMF then with 50 milliliters of cold DMF and 2×25 milliliters of methanol. The solid product was dried at 60° C. to provide 2.8 grams (56 percent) of the above product compound as dark brown light fluffy crystals.

Comparative Synthesis Example 2

A Symmetrical Perylene Bisimide Dimer

Preparation of 1,6-Bis(n-pentylimidoperyleneimido)hexane (Formula 1, R and R=n-pentyl, X-Y=1,6-hexamethylene):

Pentylimidoperylene monoanhydride (Formula 2, R=n-pentyl; 2.40 grams, 0.0050 mole) and 1,6-diaminohexane (0.232 grams, 0.0020 mole) were stirred in 100 milliliters of NMP for 1 hour at room temperature. The mixture was then heated to reflux (202° C.) for 3 hours, was cooled to 150° C., and was then filtered through a preheated 9 centimeter glass fiber filter (Whatman Grade GF/F). The solid product was then washed with 3×100 milliliter portions of boiling DMF, then with 50 milliliters of cold DMF, followed by 2×25 milliliter portions of 5 percent aqueous potassium hydroxide and finally with 4×25 milliliters of water. The product was dried at 60° C. to provide 2.0 grams (97 percent) of the above symmetrical dimer product as a dark brown solid.

Preparation of Dispersions of Unsymmetrical Perylene Bisimide Dimers in Poly(vinyl acetate):

To demonstrate the application of the invention unsymmetrical dimers as dispersed colorants, sample of pigments dispersed in poly(vinyl acetate) were prepared as follows: 0.2 gram of perylene pigment, 8 milliliters of a 1.5 percent W/W solution of poly(vinyl acetate) ($M_w$=45,000; Polysciences, Inc.) in dichloromethane and 70 grams of ⅛ inch diameter stainless balls were charged into a 30 milliliter glass jar. The jar was sealed and the mixture was milled on a roll mill for 3 to 5 days until the pigment particles were submicron, below 1 micron in diameter size, and were finely dispersed. Colored films were prepared by coating a clear plastic sheet, such as MYLAR® polyester with the dispersion using a #8 wire-wound rod. The nominal film wet thickness was about 20 microns, and the dried film was about 1 micron. The films, comprised of about 60 percent of well-dispersed pigment in PVA, had an optical density of about 1 and exhibited a variety of colors.

The large range of colors available by varying the R and X-Y groups of the unsymmetrical dimers of this invention is illustrated in Table 1, and which table provides the color of films prepared from five representative compounds.

TABLE 1

Colors of Raw Pigments And PVA-Dispersed Films of Some Unsymmetrical Perylene Bisimide Dimers

| R | X—Y | Color of Raw Pigment | Color of PVA Dispersion |
|---|---|---|---|
| n-propyl | a-4-tolyl | black | brown |
| n-propyl | b-4-phenethyl | red-brown | red |
| n-pentyl | 2-methyl-1,5-pentamethylene | brown | red-brown |
| n-butyl | benzanilide-4,4'-diyl | red-brown | orange |
| n-pentyl | diphenyl ether-3,4'-diyl | red | magenta |

Xerographic Evaluation of Unsymmetrical Perylene Bisimide Dimers:

Photoresponsive imaging members were fabricated with the unsymmetrical perylene dimer pigments obtained by Synthesis Examples 1, 3, 4, 5 and 7, respectively, and from the Comparative Synthesis Examples 1 and 2, representing the monomeric perylene bisimide and the symmetrical bisimide dimer corresponding to Synthesis Example 2. These photoresponsive, or photoconductive imaging members are generally known as dual layer photoreceptors containing a photogenerator layer, and thereover a charge transport layer. The photogenerator layer was prepared from a pigment dispersion as follows: 0.2 gram of the perylene dimer pigment was mixed with 0.05 gram of polyvinylcarbazole (PVK) polymer and 8.1 milliliters of methylene chloride in a 30 milliliter glass bottle containing 70 grams of ⅛-inch stainless steel balls. The bottle was placed on a roller mill and the dispersion was milled for 4 days. Using a film applicator of 1.5 mil gap, the pigment dispersion was coated to form the photogenerator layer on a titanized MYLAR® substrate of 75 microns in thickness, which had a gamma amino propyl triethoxy silane layer, 0.1 micron in thickness, thereover, and E.I. DuPont 49,000 polyester adhesive thereon in a thickness of 0.1 micron. Thereafter, the photogenerator layer formed was dried in a forced air oven at 135° C. for 20 minutes. Photogenerator layers for each device were each overcoated with an amine charge transport layer prepared as follows. A transport layer solution was made by mixing 8.3 grams of MAKROLON™, a polycarbonate resin, 4.4 grams of N,N'-diphenyl-N,N'-bis(3-methylphenyl)-(1,1'-biphenyl)-4,4'-diamine and 82.3 grams of methylene chloride. The solution was coated onto the above photogenerating layer using a film applicator of 10 mil gap. The resulting members were dried at 135° C. in a forced air oven for 20 minutes. The final dried thickness of transport layer was 20 microns.

The xerographic electrical properties of each imaging member were then determined by electrostatically charging its surface with a corona discharging device until the surface potential, as measured by a capacitively coupled probe attached to an electrometer, attained an initial value $V_0$. After resting for 0.5 second in the dark, the charged member reached a surface potential of $V_{ddp}$, dark development potential, and was then exposed to light from a filtered xenon lamp. A reduction in the surface potential to $V_{bg}$, background potential due to photodischarge effect, was observed. The dark decay in volt/second was calculated as $(V_0-V_{ddp})/0.5$. The lower the dark decay value, the superior is the ability of the member to retain its charge prior to exposure by light. Similarly, the lower the $V_{ddp}$, the poorer is the charging behavior of the member. The percent photodischarge was calculated as 100 percent×$(V_{ddp}-V_{bg})/V_{ddp}$. The light energy used to photodischarge the imaging member during the exposure step was measured with a light meter. The photosensitivity of the imaging member can be described in terms of $E_{1/2}$, amount of exposure energy in erg/cm² required to achieve 50 percent photodischarge from the dark development potential. The higher the photosensitivity, the smaller the $E_{1/2}$ value. High photosensitivity (lower $E_{1/2}$ value), lower dark decay and high charging are desired for the improved performance of xerographic imaging members.

The following Table 2 summarizes the xerographic electrical results when the exposed light used was at a wavelength of 500 nanometers.

TABLE 2

| Imaging Member No. | Perylene Dimer | Synthesis Example | Dark Decay V/s | $E_{1/2}$ erg/cm² |
|---|---|---|---|---|
| 1 | 1,5-Bis(n-butyl-imidoperyleneimido)-2-methylpentane | 1 | 27.6 | 8.0 |
| 2 | 1,5-Bis(n-pentyl-imidoperyleneimido)-2-methylpentane | 2 | 35.8 | 4.3 |
| 3 | a-4-Bis(n-butylimidoperyleneimido) toluene | 4 | 15.8 | 19 |
| 4 | b-4-Bis(n-pentylimidoperyleneimido) ethylbenzene | 5 | 31 | 14 |
| 5 | 3,4'-Bis(n-pentylimidoperyleneimido) diphenyl ether | 7 | 34.6 | 7.6 |
| 6 | N,N'-Bis(n-pentyl)perylene-3,4,9,10-tetracarboxylic acid dicarboximide | Comparative Synthesis Example 1 | 1.2 | 6.7 |
| 7 | 1,6-Bis(n-pentylimidoperyleneimido) hexane | Comparative Synthesis Example 2 | 49.4 | 8.9 |

All the imaging members with the invention unsymmetrical photogenerating pigments exhibited acceptable charge acceptance, and most showed low to moderate dark decay ranging from about 20 to <50 volts per second, and photosensitivities ranging from excellent ($E_{1/2}$ of about 4.3 ergs/cm²) to moderate ($E_{1/2}$ of about 19 ergs/cm²) indicating that these unsymmetrical perylene dimers would be very useful for xerographic imaging applications. There does not appear to be an empirical or theoretical correlation between the chemical structures of the perylene pigments and their efficacies as photogenerator pigments for xerographic imaging applications. However, the much higher sensitivity ($E_{1/2}$=4.3 ergs/cm²) observed for the unsymmetrical dimer of Example 2, compared to the related n-pentyl monomeric perylene bisimide of Comparative Example 1 ($E_{1/2}$=6.7) and the related symmetrical dimer of Comparative Example 2 ($E_{1/2}$=8.9), which has a 6-carbon symmetrical bridging group instead of the unsymmetrical 6-carbon bridge of Example 2, indicates that the unsymmetrical dimers of this invention possess unique xerographic electrical properties.

Other embodiments and modifications of the present invention may occur to those skilled in the art subsequent to a review of the information presented herein; these embodiments, modifications, and equivalents thereof, are also included within the scope of the present invention.

What is claimed is:

1. Unsymmetrical perylene dimers

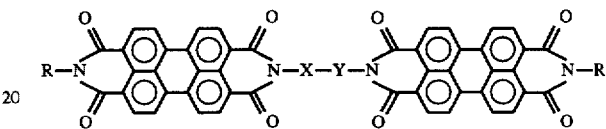

wherein R is hydrogen, alkyl, cycloalkyl, substituted alkyl, aryl, substituted aryl, aralkyl or substituted aralkyl group, and X-Y is a bridging moiety selected from alkylene, substituted alkylene, arylene, substituted arylene, aralkylene or substituted aralkylene wherein said bridging moiety is unsymmetrical.

2. A perylene pigment in accordance with claim 1 wherein alkyl contains from 1 to about 25 carbon atoms, aryl contains from 6 to about 24 carbon atoms, and aralkyl contains from 7 to about 30 carbon atoms.

3. A perylene pigment in accordance with claim 1 wherein R is hydrogen, and alkyl is methyl, ethyl, propyl, butyl, isobutyl, sec-butyl, 2-methylbutyl, 3-methylbutyl, n-pentyl, 2-pentyl, 3-pentyl, neopentyl, n-hexyl, n-heptyl n-octyl, n-nonyl or n-decyl, or wherein R is hydrogen, methyl, ethyl, n-propyl, 3-methoxypropyl, n-butyl, isobutyl, n-pentyl, 2-pentyl, 3-pentyl, 2-methylbutyl, 3-methylbutyl, neopentyl, n-hexyl, n-heptyl, n-octyl, benzyl, 3-chlorobenzyl or phenethyl, and X-Y is 1,2-propylene, butane-1,2-diyl, butane-1,3-diyl, pentane-1,3-diyl, pentane-1,4-diyl, 2-methylbutane-1,4-diyl, hexane-1,5-diyl, or 2-methylpentane-1,5-diyl.

* * * * *